United States Patent
Hsieh et al.

(10) Patent No.: US 11,371,009 B2
(45) Date of Patent: Jun. 28, 2022

(54) IN VITRO CELL CULTURE PLATFORM AND CELL CULTURE METHOD

(71) Applicant: NATIONAL TSING HUA UNIVERSITY, Hsinchu (TW)

(72) Inventors: Hsin-Lin Hsieh, Hsinchu (TW); Jen-Huang Huang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 708 days.

(21) Appl. No.: 16/193,346

(22) Filed: Nov. 16, 2018

(65) Prior Publication Data

US 2020/0131466 A1  Apr. 30, 2020

(30) Foreign Application Priority Data

Oct. 30, 2018  (TW) ................................. 107138412

(51) Int. Cl.
*C12M 1/36* (2006.01)
*C12M 1/12* (2006.01)
*C12M 1/00* (2006.01)

(52) U.S. Cl.
CPC ............ *C12M 41/48* (2013.01); *C12M 25/02* (2013.01); *C12M 25/06* (2013.01); *C12M 29/00* (2013.01)

(58) Field of Classification Search
None
See application file for complete search history.

(56) References Cited

U.S. PATENT DOCUMENTS 10,988,723 B1 * 4/2021 Hatch .................... C12M 23/44

FOREIGN PATENT DOCUMENTS

| CN | 102864078 A | 1/2013 | |
|---|---|---|---|
| CN | 103667054 A | 3/2014 | |
| CN | 104560711 A | 4/2015 | |
| WO | WO-2016049365 A1 * | 3/2016 | ........ B01L 3/502715 |

OTHER PUBLICATIONS

Hsin-Lin Hsieh et al., "Fabrication Of Human Bronchial Epithelium Culture Platform For Inhalation Drug Development", 65th TwIChE Annual Meeting, dated on Nov. 9-10, 2018, poster, Taiwan, R.O.C.

* cited by examiner

Primary Examiner — William H. Beisner
(74) Attorney, Agent, or Firm — Fay Sharpe LLP

(57) ABSTRACT

An automatic in vitro cell culture platform includes a fluid storage device, a channel control panel, a cell culture chip and a fluid drive unit. The fluid storage device is for storing a cell culture medium and a waste liquid. The channel control panel is pipe-connected to the fluid storage device. The cell culture chip is disposed on the channel control panel and is for culturing a cell. The fluid drive unit is pipe-connected to the channel control panel and is for driving the cell culture medium and the waste liquid to flow between the fluid storage device and the cell culture chip through the channel control panel.

16 Claims, 16 Drawing Sheets
(3 of 16 Drawing Sheet(s) Filed in Color)

IN VITRO CELL CULTURE PLATFORM AND CELL CULTURE METHOD

RELATED APPLICATIONS

This application claims priority to Taiwan Application Serial Number 107138412, filed Oct. 30, 2018, which is herein incorporated by reference.

BACKGROUND

Technical Field

The present disclosure relates to an in vitro cell culture platform. More particularly, the present disclosure relates to an in vitro cell culture platform which can be used for culturing cells automatically.

Description of Related Art

The researching and developing of novel drugs are in full swing in the modern society with high development of science and technology. In the process of drug development, the target drug must be tested by the preclinical studies so as to confirm the efficacy and the commercial value thereof before the clinical trials of the human body. However, unprecedented challenges, such as increasing the costs of drug development but reducing the test efficiency thereof, have occurred in both of the preclinical studies or the clinical trials.

In the preclinical studies, the target drug should be tested by cell experiments and then applied to experimental animals so as to confirm the pharmacological properties and the biosafety thereof. When performing the cell experiments, the experimental operating methods may be different between different operators. Thus, the experimental results thereof may differ from the actual pharmacological properties of the target drug and further affect the accuracy of the following animal experiments. Furthermore, during the cell culture, the cell culture medium must be replaced every predetermined incubation time so as to remove the waste generated from the cell metabolism as well as provide nutrients needed for cell growth. Consequently, it not only necessary to spend manpower and time to replace the cell culture medium, but the cell culture medium may be contaminated due to the introduction of the exogenous microorganisms during the replacing process thereof. Thus, the experimental results of the cell experiments may be affected. Furthermore, because the physiological conditions of experimental animals are quite different from those of human beings, the results of animal experiments could have failed to reflect the efficacy of the target drug applied to human beings accurately during animal experiments. Moreover, there are also many moral disputes of using live experimental animals for experiments.

In clinical trials, although the pharmacological properties and biosafety of the target drug have been evaluated by the animal experiments and other preclinical studies first, the results of the clinical trials may be inconsistent to the actual condition due to the incorrect results of the preclinical studies. Even worse, it could lead to the failure of the clinical trials. Accordingly, not only research costs are wasted, but it can also cause irreparable physiological injury to subjects in the clinical trials.

Therefore, how to provide a cell culture platform with low cost and high stability so as to apply to the drug testing with high-accuracy, and how to provide a more reliable predictive ability of drug efficacy and biosafety, have become the major aims of related academic and industry.

SUMMARY

According to one aspect of the present disclosure, an automatic in vitro cell culture platform includes a fluid storage device, a channel control panel, a cell culture chip and a fluid drive unit. The fluid storage device includes a first fluid storage unit and a second fluid storage unit. The first fluid storage unit is for storing a cell culture medium. The second fluid storage unit is disposed adjacent to the first fluid storage unit and is for storing a waste liquid. The channel control panel is pipe-connected to the fluid storage device and includes a valve group, wherein the valve group is for controlling a transport of the cell culture medium and the waste liquid. The cell culture chip is disposed on the channel control panel and is pipe-connected thereto, and the cell culture chip includes an upper chamber, a lower chamber and a porous semipermeable membrane. The upper chamber is for culturing a cell. The lower chamber is disposed under the upper chamber and is for accommodating the cell culture medium. The porous semipermeable membrane is disposed between the upper chamber and the lower chamber, wherein the cell culture medium can flow between the upper chamber and the lower chamber through the porous semipermeable membrane, and a liquid level of the cell culture medium in the cell culture chip is higher than a level of the porous semipermeable membrane in the cell culture chip. The fluid drive unit is pipe-connected to the channel control panel and is for driving the cell culture medium and the waste liquid to flow between the fluid storage device and the cell culture chip through the channel control panel.

According to another aspect of the present disclosure, a cell culture method includes the following steps. The automatic in vitro cell culture platform of the aforementioned aspect is provided. A washing step is performed, wherein the cell culture medium is transported from the first fluid storage unit to the cell culture chip by the fluid drive unit so as to wash the upper chamber and the lower chamber, and then the cell culture medium used to wash the upper chamber and the lower chamber is transported from the cell culture chip to the second fluid storage unit by the fluid drive unit. A cell culture medium filling step is performed, wherein the cell culture medium is transported from the first fluid storage unit to the cell culture chip by the fluid drive unit so as to fill the cell culture medium into the upper chamber and the lower chamber, respectively. A cell seeding step is performed, wherein the cell is seeded in the upper chamber for an incubation time, and the cell is attached and grows on the porous semipermeable membrane. A cell culture medium replacing step is performed, wherein the cell culture medium cultured after the incubation time is removed from the cell culture chip by the fluid drive unit, and then the cell culture medium of the first fluid storage unit is transported from the first fluid storage unit to the cell culture chip by the fluid drive unit.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DETAILED DESCRIPTION

Figure 1:
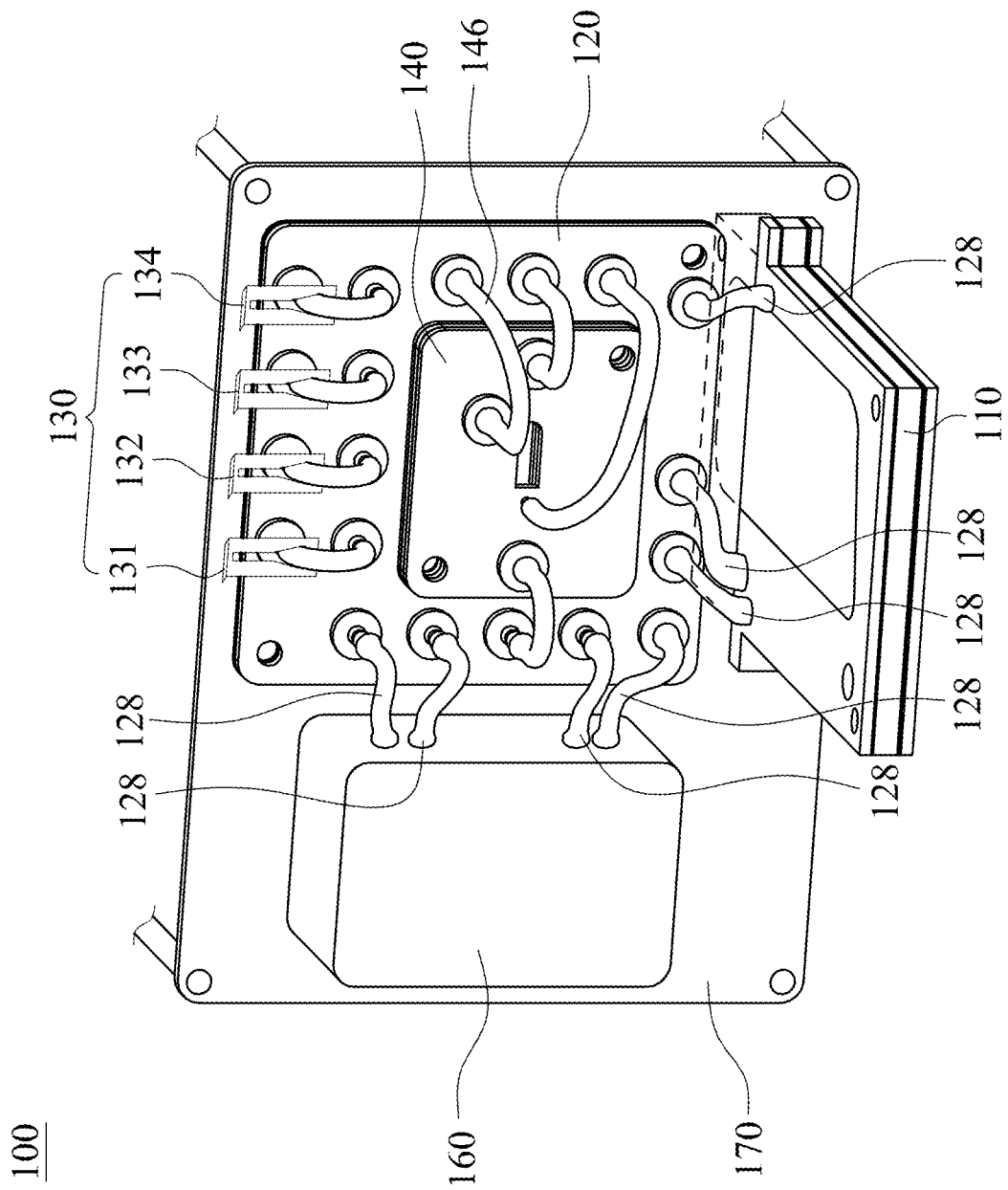
FIG. 1 is a top schematic view of an automatic in vitro cell culture platform according to one embodiment of one aspect of the present disclosure.
Figure 2:
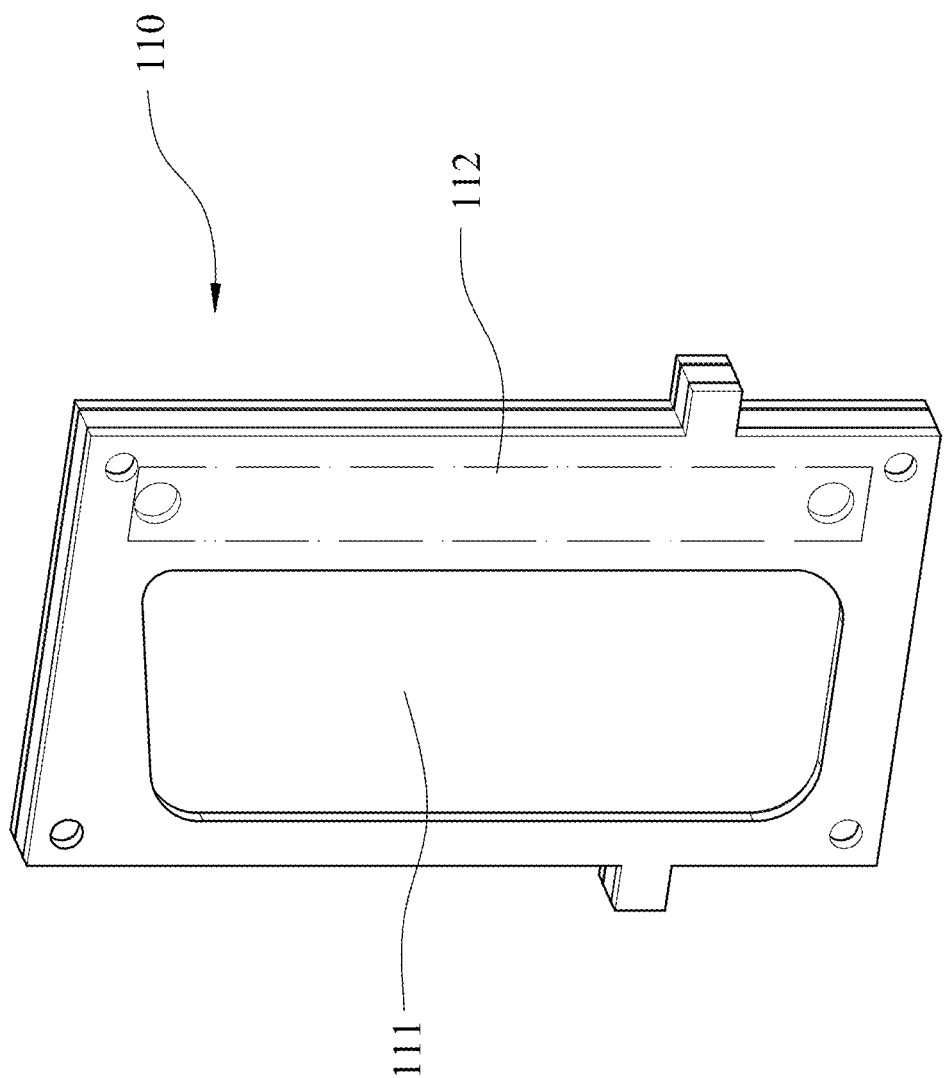
FIG. 2 is a schematic view of a fluid storage device of the automatic in vitro cell culture platform of FIG. 1.
Figure 4A:
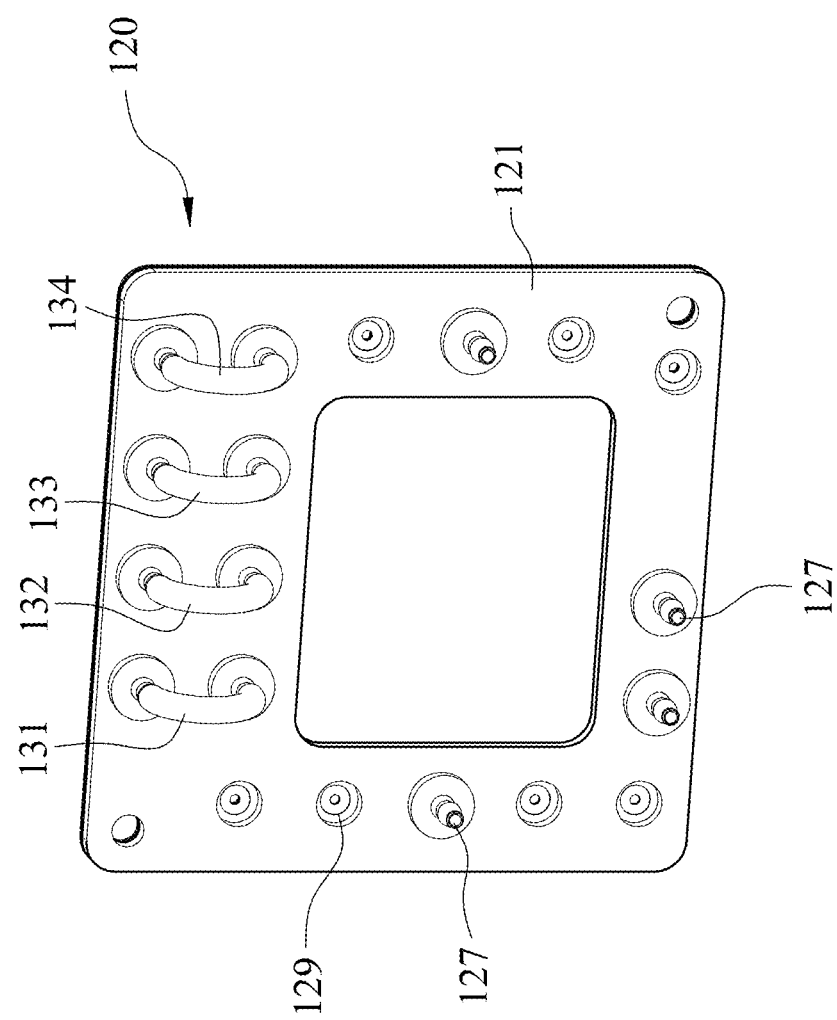
FIG. 4A is a schematic view of a channel control panel of the automatic in vitro cell culture platform of FIG. 1.
Figure 4B:
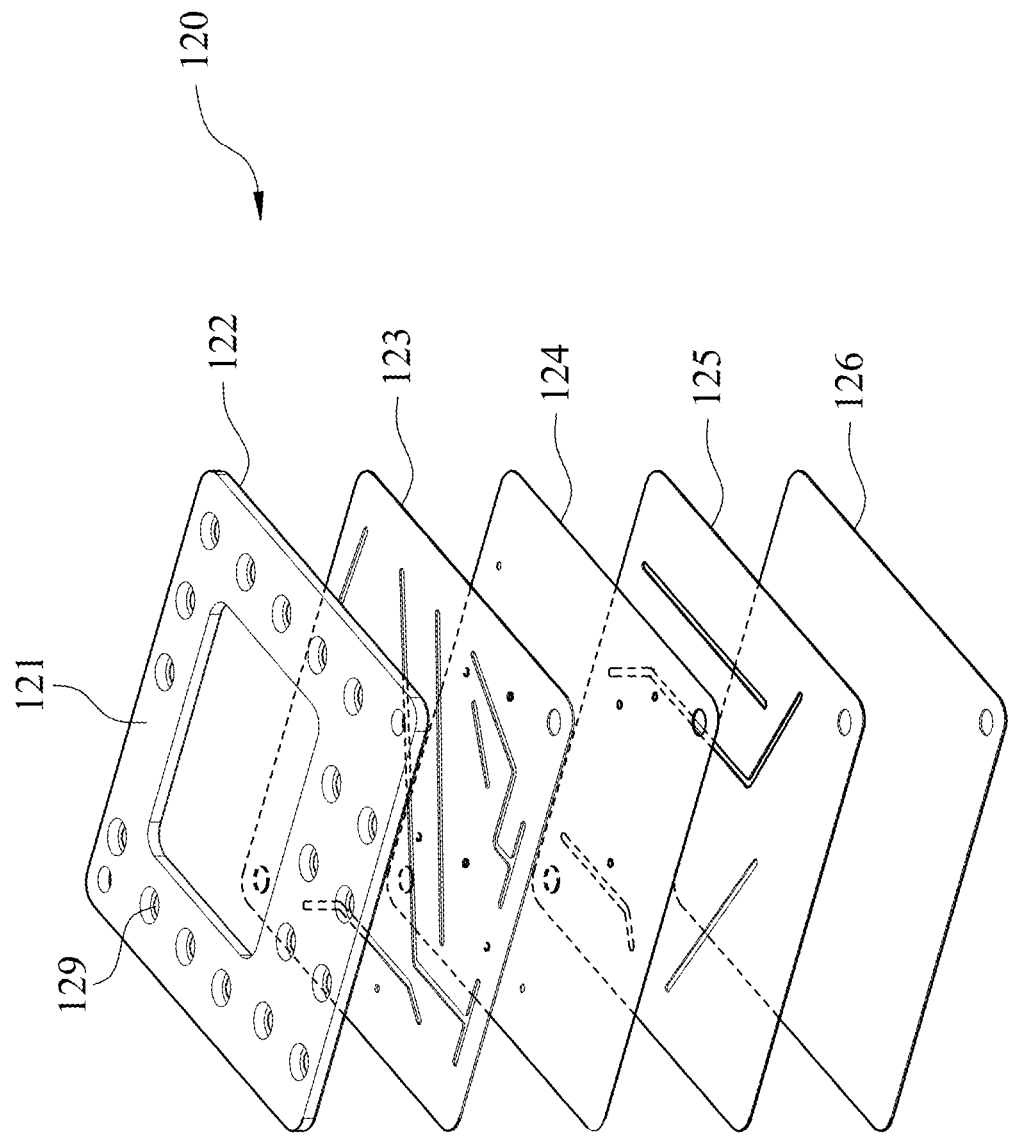
FIG. 4B is an exploded view of the channel control panel of the automatic in vitro cell culture platform of FIG. 4A.
Figure 5A:
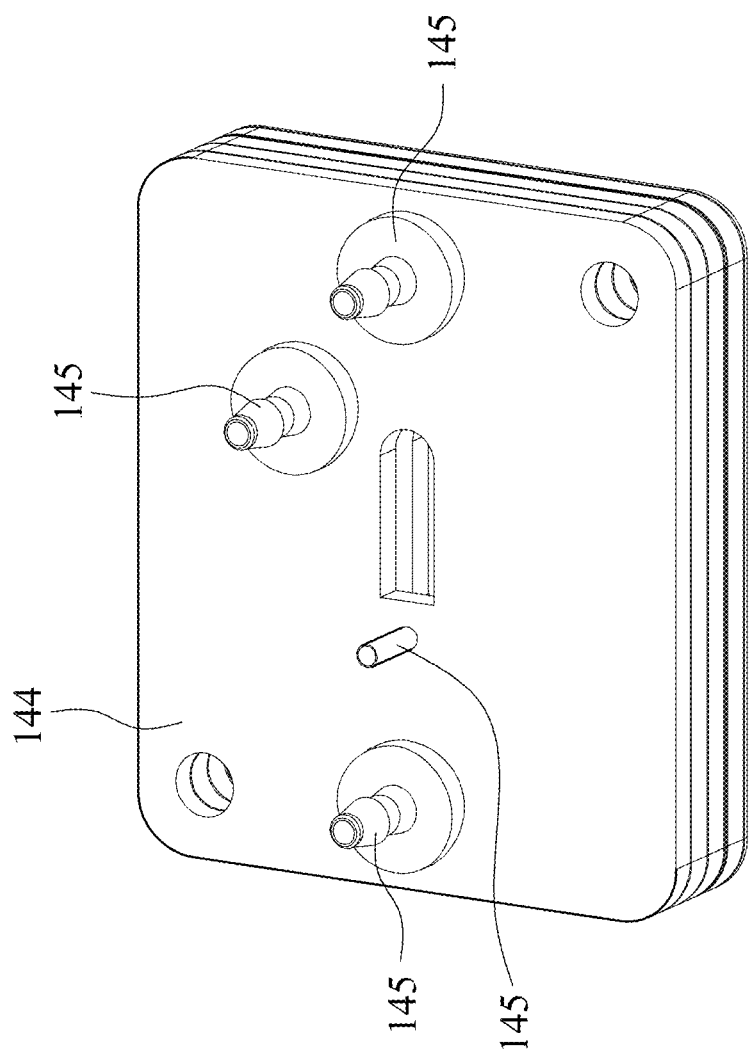
FIG. 5A is a schematic view of a cell culture chip of the automatic in vitro cell culture platform of FIG. 1.
Figure 5B:
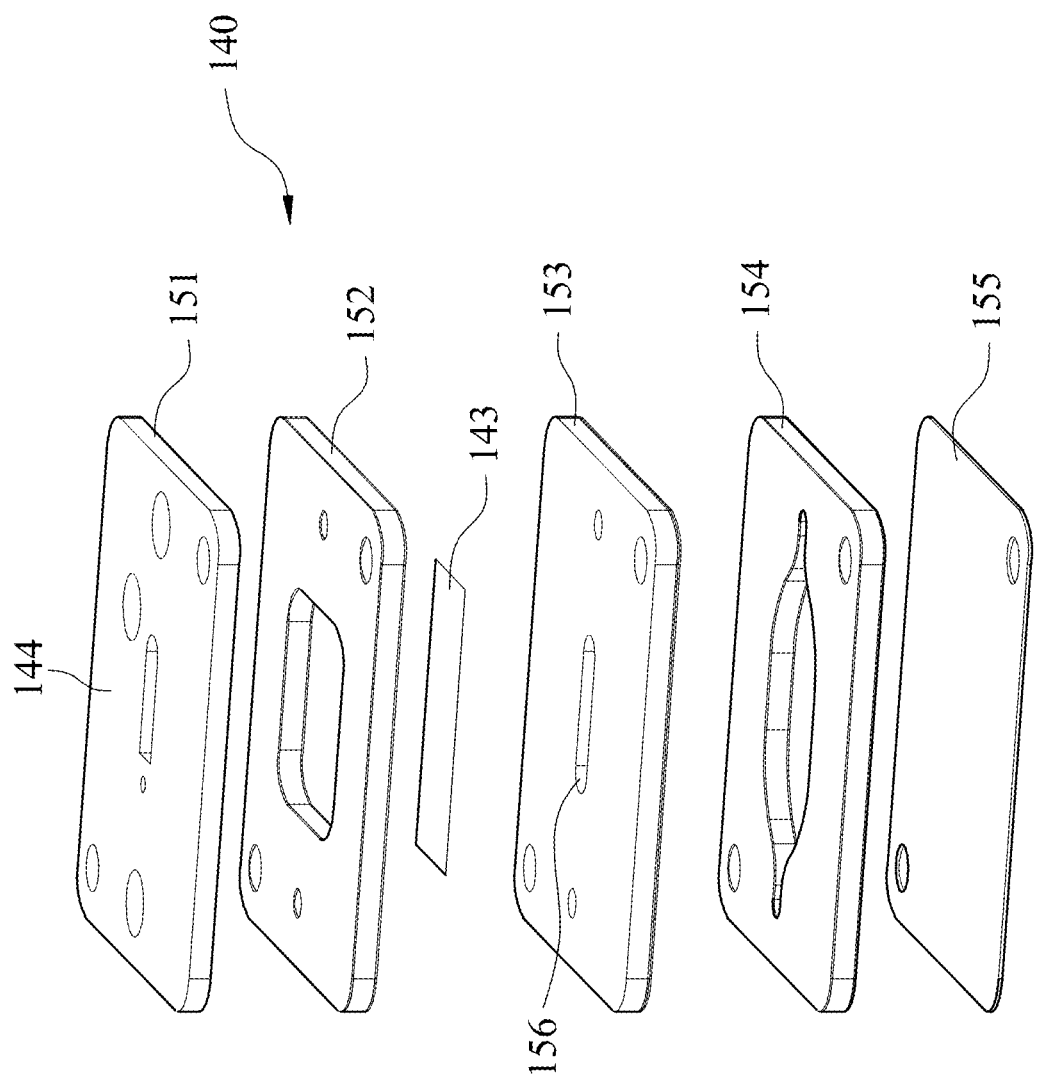
FIG. 5B is an exploded view of the cell culture chip of the automatic in vitro cell culture platform of FIG. 5A.
Figure 5C:
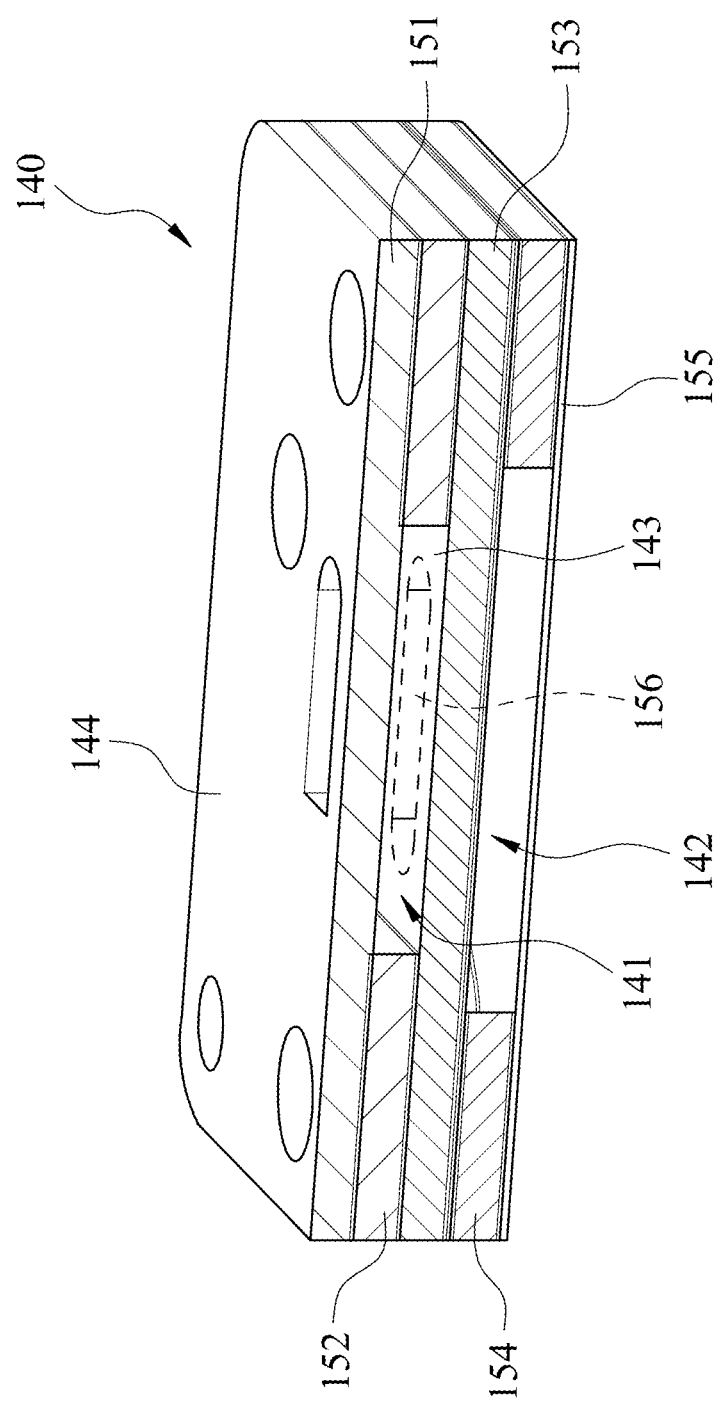
FIG. 5C is a cross-sectional view of the cell culture chip of the automatic in vitro cell culture platform of FIG. 5A.

Please refer to FIG. 1, FIG. 2, FIG. 4A, FIG. 4B, FIG. 5A, FIG. 5B and FIG. 5C. FIG. 1 is a top schematic view of an automatic in vitro cell culture platform 100 according to one embodiment of one aspect of the present disclosure. FIG. 2 is a schematic view of a fluid storage device 110 of the automatic in vitro cell culture platform 100 of FIG. 1. FIG. 4A is a schematic view of a channel control panel 120 of the automatic in vitro cell culture platform 100 of FIG. 1. FIG. 4B is an exploded view of the channel control panel 120 of the automatic in vitro cell culture platform 100 of FIG. 4A. FIG. 5A is a schematic view of a cell culture chip 140 of the automatic in vitro cell culture platform 100 of FIG. 1. FIG. 5B is an exploded view of the cell culture chip 140 of the automatic in vitro cell culture platform 100 of FIG. 5A. FIG. 5C is a cross-sectional view of the cell culture chip 140 of the automatic in vitro cell culture platform 100 of FIG. 5A. The automatic in vitro cell culture platform 100 includes the fluid storage device 110, the channel control panel 120, the cell culture chip 140 and a fluid drive unit 160.

In the embodiment of FIG. 1, the automatic in vitro cell culture platform 100 is shown in a top schematic view so as to clearly illustrate the structural arrangement of the automatic in vitro cell culture platform 100 of the present disclosure. As shown in FIG. 1, the fluid storage device 110 is disposed in a method that a long axis of the fluid storage device 110 is perpendicular to both of the long axis of the channel control panel 120 and the cell culture chip 140 so as to prevent the liquid stored in the fluid storage device 110, such as the cell culture medium and the waste liquid, from leaking from the fluid storage device 110. As shown in FIG. 2, the fluid storage device 110 includes a first fluid storage unit 111 and a second fluid storage unit 112. The first fluid storage unit 111 is for storing the cell culture medium, and the second fluid storage unit 112 is disposed adjacent to the first fluid storage unit 111 and is for storing the waste liquid. More preferably, the aforementioned cell culture medium can include a growth factor, a cell differentiation factor and other bioactive factors which can enhance the growth or the differentiation of the cell so as to facilitate the progress of the following cell culture or the experiments thereof.

In the embodiment of FIG. 2, a volume of the first fluid storage unit 111 can be 10 mL and larger than a volume of the second fluid storage unit 112 so as to store the cell culture medium needed in the cell culture as follow, but the present disclosure is not limited thereto. More preferably, although not shown in the figures, the fluid storage device 110 can further include a medium exchange port (not shown) and a waste liquid exchange port (not shown), wherein the medium exchange port is connected to the first fluid storage unit 111, and the waste liquid exchange port is connected to the second fluid storage unit 112. Therefore, it is favorable for filling the cell culture medium and for circulating and discharging the waste liquid.

Figure 3:
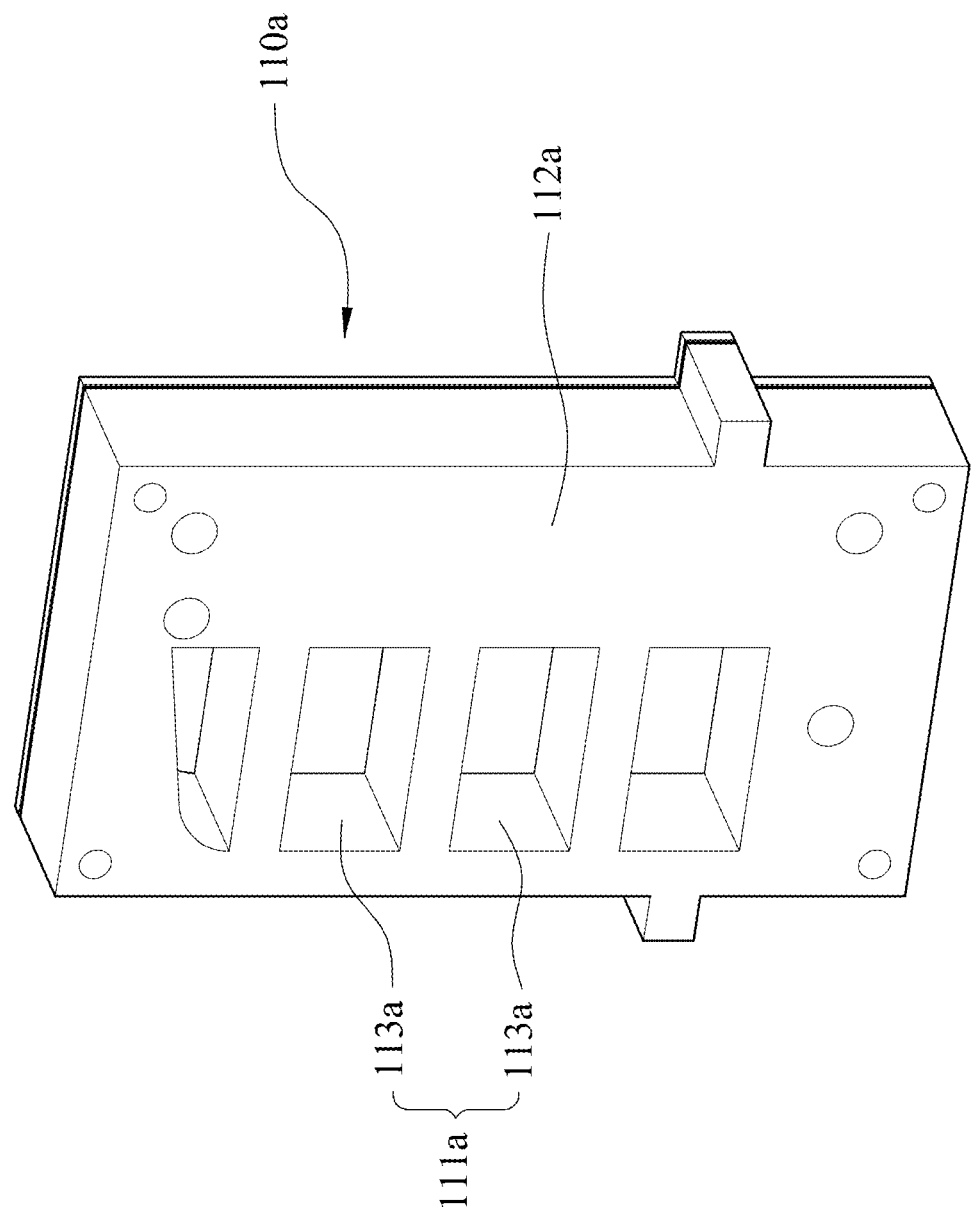
FIG. 3 is a schematic view of another fluid storage device of the automatic in vitro cell culture platform of FIG. 1.

Please refer to FIG. 3, which is a schematic view of another fluid storage device 110a of the automatic in vitro cell culture platform 100 of FIG. 1. As shown in FIG. 3, the fluid storage device 110a includes a first fluid storage unit 111a and a second fluid storage unit 112a, wherein the first fluid storage unit 111a can further include a plurality of fluid storage subunits 113a. The fluid storage subunits 113a are separately disposed in the first fluid storage unit 111a so as to store different types of cell culture medium or to collect the replaced cell culture medium. Therefore, it is favorable for progressing the following experiments.

Please refer to FIG. 1, FIG. 4A and FIG. 4B simultaneously, the channel control panel 120 is pipe-connected to the fluid storage device 110 and includes a valve group 130, wherein the valve group 130 is for controlling a transport of the cell culture medium and the waste liquid. More preferably, the valve group 130 can include a plurality of valve elements. In the embodiment of FIG. 1, a number of the valve elements can be four, those are a first valve element 131, a second valve element 132, a third valve element 133 and a fourth valve element 134. The first valve element 131, the second valve element 132, the third valve element 133 and the fourth valve element 134 are for controlling the transport of the cell culture medium and the waste liquid, respectively, but the present disclosure is not limited thereto.

More preferably, as shown in FIG. 1, FIG. 4A and FIG. 4B, the channel control panel 120 can have a tube connection surface 121 and include, in order from the tube connection surface 121 to a bottom of the channel control panel 120, a tube connection plate 122, a first channel base plate 123, a second channel base plate 124, a third channel base plate 125 and a bottom plate 126, wherein the tube connection plate 122, the first channel base plate 123, the second channel base plate 124, the third channel base plate 125 and the bottom plate 126 are sequentially stacked so as to form a plurality of microchannels (reference numbers are omitted)

for transporting the cell culture medium and the waste liquid. Furthermore, the tube connection plate 122, the first channel base plate 123, the second channel base plate 124, the third channel base plate 125 and the bottom plate 126 can be made by a laser cutting method. Therefore, it is favorable for cutting quickly and accurately. Moreover, the tube connection plate 122, the first channel base plate 123, the second channel base plate 124, the third channel base plate 125 and the bottom plate 126 can be made of different resin polymer materials according to actual needs, so that the manufacturing efficiency thereof can be enhanced and it is favorable for mass production.

Furthermore, the channel control panel 120 can further include a plurality of channel ports 127 (reference number is shown in FIG. 4A) and a plurality of connecting tubes 128 (reference numbers are shown in FIG. 1). The channel ports 127 are separately disposed on the tube connection surface 121. One end of each of the connecting tubes 128 is connected correspondingly to one of the channel ports 127, and the other end of each of the connecting tubes 128 is connected to the fluid drive unit 160 or the fluid storage device 110. Therefore, it is favorable for transporting the cell culture medium and the waste liquid by the microchannels of the channel control panel 120 through the connecting tubes 128. In detail, the tube connection surface 121 of the channel control panel 120 is disposed on the tube connection plate 122, a channel opening 129 of each of the microchannels is disposed on the tube connection surface 121 (there is only one reference number of the channel openings 129 shown in FIG. 4A and FIG. 4B), and each of the channel ports 127 is correspondingly disposed to one channel opening 129 and is for arranging the connecting tube 128. More preferably, in the embodiment of FIG. 1, a number of the connecting tubes 128 for connecting the channel control panel 120 to the fluid drive unit 160 is four, a number of the connecting tubes 128 for connecting the channel control panel 120 to the fluid storage device 110 is three, but the present disclosure is not limited thereto.

Please refer to FIG. 1, FIG. 5A, FIG. 5B and FIG. 5C simultaneously, the cell culture chip 140 is disposed on the channel control panel 120 and pipe-connected thereto, and the cell culture chip 140 includes an upper chamber 141, a lower chamber 142 and a porous semipermeable membrane 143. The upper chamber 141 is for culturing a cell, the lower chamber 142 is disposed under the upper chamber 141 and is for accommodating the cell culture medium, and the porous semipermeable membrane 143 is disposed between the upper chamber 141 and the lower chamber 142, wherein the cell culture medium can flow between the upper chamber 141 and the lower chamber 142 through the porous semipermeable membrane 143, and a liquid level of the cell culture medium in the cell culture chip 140 is higher than a level of the porous semipermeable membrane 143 in the cell culture chip 140.

More preferably, as shown in FIG. 1, FIG. 5A, FIG. 5B and FIG. 5C, the cell culture chip 140 can have a pipe connection surface 144 and include, in order from the pipe connection surface 144 to a bottom of the cell culture chip 140, a first base plate 151, a second base plate 152, a third base plate 153, a fourth base plate 154 and a resin sheet 155, wherein the first base plate 151, the second base plate 152 and the third base plate 153 are sequentially stacked so as to form the upper chamber 141, and the third base plate 153, the fourth base plate 154 and the resin sheet 155 are sequentially stacked so as to form the lower chamber 142. The third base plate 153 includes an opening 156, and the porous semipermeable membrane 143 is disposed and covered on the opening 156. Particularly, the third base plate 153 forms the bottom surface of the upper chamber 141 and the top surface of the lower chamber 142. Therefore, the lower chamber 142 can be stacked disposed under the upper chamber 141. Furthermore, because the porous semipermeable membrane 143 is disposed and covered on the opening 156, the cell can attach and grow on the porous semipermeable membrane 143. Therefore, it is favorable for exchanging the cell culture medium of the upper chamber 141 with the cell culture medium of the lower chamber 142, and the liquid level of the cell culture medium in the cell culture chip 140 can be adjusted according to the cell culture conditions or the experimental requirements. Accordingly, a surface of the cell layer in the cell culture chip 140 can expose to the air so as to facilitate the differentiation of the cell and progressing the experiments, and an attached surface of the cell layer in the cell culture chip 140 can directly contact to the cell culture medium of the lower chamber 142 so as to absorb the nutrient thereof. More preferably, an average pore size of the porous semipermeable membrane 143 can range from 0.2 μm to 8 μm, so that the user can select a porous semipermeable membrane 143 with different average pore sizes according to actual needs. Therefore, the automatic in vitro cell culture platform 100 of the present disclosure can be used for culturing different types of cells or for progressing different cell experiments so that the application breadth of the automatic in vitro cell culture platform 100 of the present disclosure can be expanded.

Furthermore, the cell culture chip 140 can further include at least four pipe ports 145 (reference numbers are shown in FIG. 5A) and at least four infusion tubes 146 (reference number is shown in FIG. 1). The four pipe ports 145 are separately disposed on the pipe connection surface 144, wherein two of the pipe ports 145 are connected to the upper chamber 141, and the other two of the pipe ports 145 are connected to the lower chamber 142. One end of each of the infusion tubes 146 is connected correspondingly to one of the pipe ports 145, and the other end of each of the infusion tubes 146 is connected correspondingly to the channel control panel 120. Therefore, it is favorable for transporting the cell culture medium or the waste liquid to the fluid storage device 110 through the channel control panel 120. More preferably, the first base plate 151, the second base plate 152, the third base plate 153, the fourth base plate 154 and the resin sheet 155 can be made by a laser cutting method. Therefore, it is favorable for cutting quickly and accurately. Furthermore, the first base plate 151, the second base plate 152, the third base plate 153, the fourth base plate 154 and the resin sheet 155 can be made of different resin polymer materials according to actual needs, so that the manufacturing efficiency thereof can be enhanced and it is favorable for mass production.

In the embodiment of FIG. 1, the fluid drive unit 160 is pipe-connected to the channel control panel 120 and is for driving the cell culture medium and the waste liquid to flow between the fluid storage device 110 and the cell culture chip 140 through the channel control panel 120. More preferably, the fluid drive unit 160 can be a peristaltic pump. The peristaltic pump can transport the liquid by pressing and releasing the peristaltic tubes (not shown) thereof by turns, and the liquid therein can be isolated within the peristaltic tubes without contact with other elements of the peristaltic pump. Therefore, the peristaltic pump has an advantage of low contaminate rate, and it is favorable for preventing the automatic in vitro cell culture platform 100 from contamination during the cell culture or cell experiments.

Furthermore, in the embodiment of FIG. 1, the automatic in vitro cell culture platform 100 can further include a basal board 170. The basal board 170 is for loading the fluid storage device 110, the channel control panel 120, the cell culture chip 140 and the fluid drive unit 160, but the present disclosure is not limited thereto.

Therefore, in the automatic in vitro cell culture platform 100 of the present disclosure, the cell culture medium can be transported automatically among the fluid storage device 110, the channel control panel 120 and the cell culture chip 140 by the fluid drive unit 160. It can not only eliminate the steps for changing the cell culture medium manually during cell culture or the experiment so as to prevent the difference of cell culture state or contamination caused by human manipulation but also enhance safety, efficiency and stability of cell culture. Thus, the automatic in vitro cell culture platform 100 of the present disclosure can be further applied in the fields of cell culture, drug development and drug safety testing, and the market value thereof is also excellent.

Figure 6:
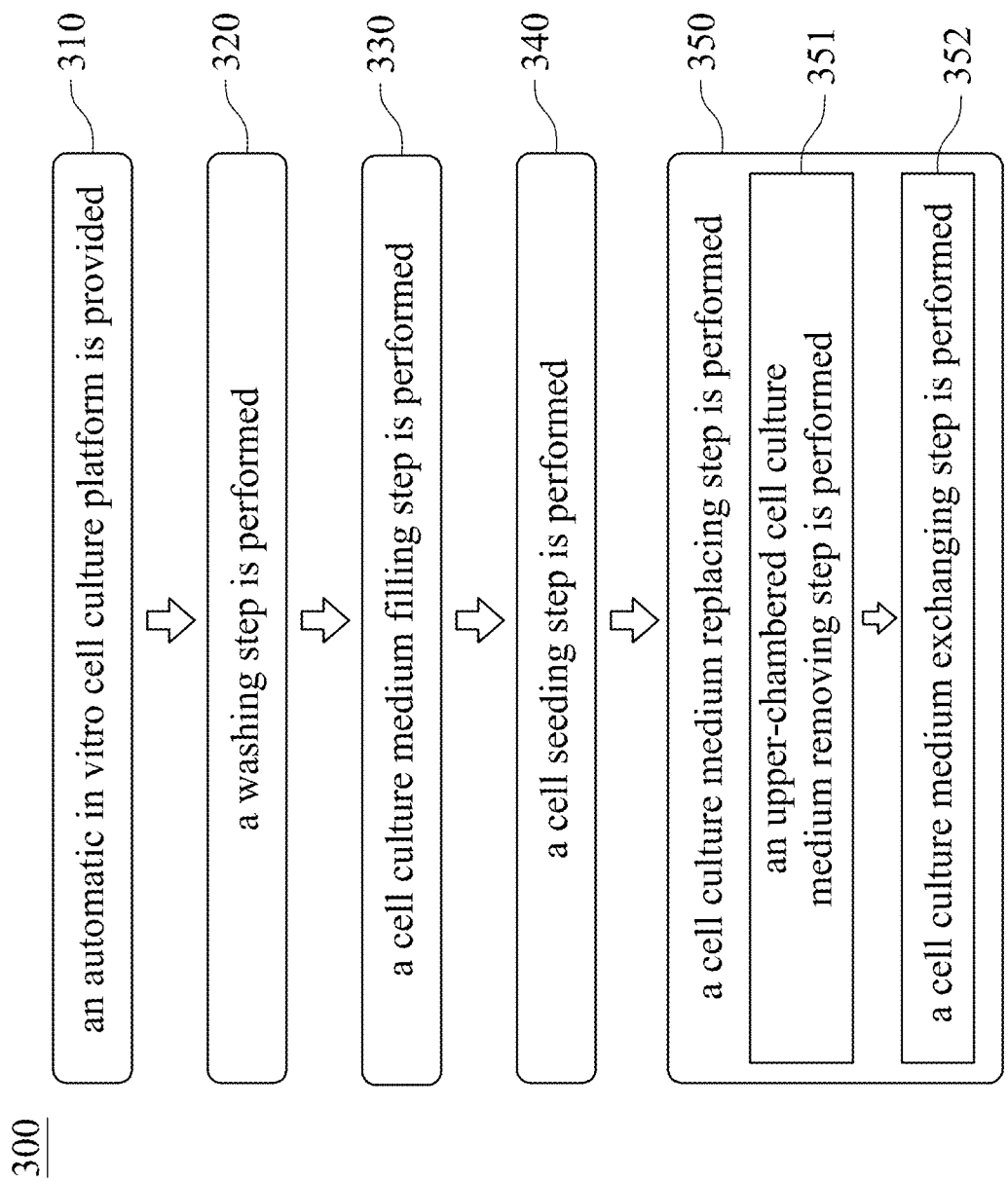
FIG. 6 is a flow chart of a cell culture method according to one embodiment of another aspect of the present disclosure.

Please refer to FIG. 1 and FIG. 6 simultaneously, wherein FIG. 6 is a flow chart of a cell culture method 300 according to one embodiment of another aspect of the present disclosure. The cell culture method 300 includes Step 310, Step 320, Step 330, Step 340 and Step 350.

In Step 310, an automatic in vitro cell culture platform is provided. More preferably, in the embodiment of FIG. 6, the aforementioned automatic in vitro cell culture platform can be the automatic in vitro cell culture platform 100 of the embodiment of FIG. 1 so as to be applied in the cell culture subsequently.

In Step 320, a washing step is performed, wherein the cell culture medium is transported from the first fluid storage unit 111 (reference number is shown in FIG. 2) to the cell culture chip 140 by the fluid drive unit 160 so as to wash the upper chamber 141 (reference number is shown in FIG. 5C) and the lower chamber 142 (reference number is shown in FIG. 5C), and then the cell culture medium used to wash the upper chamber 141 and the lower chamber 142 is transported from the cell culture chip 140 to the second fluid storage unit 112 (reference number is shown in FIG. 2) by the fluid drive unit 160. In other words, the cell culture medium will convert into the aforementioned waste liquid after being used to wash the upper chamber 141 and the lower chamber 142, and the waste liquid can be transported to the second fluid storage unit 112 by the fluid drive unit 160 and then be discharged from the second fluid storage unit 112.

In Step 330, a cell culture medium filling step is performed, wherein the cell culture medium is transported from the first fluid storage unit 111 to the cell culture chip 140 by the fluid drive unit 160 so as to fill the cell culture medium into the upper chamber 141 and the lower chamber 142, respectively. Therefore, the cell culture medium can provide nutrients needed for the growth of cell subsequently.

In Step 340, a cell seeding step is performed, wherein the cell is seeded in the upper chamber 141 for an incubation time, and the cell is attached and grows on the porous semipermeable membrane 143. In detail, before the cell seeding step is performed, macromolecules such as collagen and poly-amino acid will be coated on the surface of the porous semipermeable membrane 143 so as to facilitate the cell to attach and grow thereon. Furthermore, because the porous semipermeable membrane 143 is disposed between the upper chamber 141 and the lower chamber 142, the cell culture medium can flow between the upper chamber 141 and the lower chamber 142 through the porous semipermeable membrane 143, so that it is favorable for enhancing the proliferation and the differentiation of the cell during the following cell culture. Moreover, the aforementioned incubation time can be a doubling time of different cells or a period of time set by the user, but the present disclosure is not limited thereto.

In Step 350, a cell culture medium replacing step is performed, wherein the cell culture medium cultured after the incubation time is removed from the cell culture chip 140 by the fluid drive unit 160, and then the cell culture medium of the first fluid storage unit 111 is transported from the first fluid storage unit 111 to the cell culture chip 140 by the fluid drive unit 160. More preferably, in the embodiment of FIG. 6, Step 350 can further include Step 351 and Step 352.

In Step 351, an upper-chambered cell culture medium removing step is performed, wherein the cell culture medium cultured after the incubation time is transported from the upper chamber 141 to the second fluid storage unit 112 by the fluid drive unit 160, and then the cell culture medium of the first fluid storage unit 111 is transported to the cell culture chip 140 by the fluid drive unit 160. Therefore, the cell culture medium including cell metabolites, aging cells and other wastes can be removed so that a new cell culture medium can be further added so as to provide enough nutrients needed for cell growth.

In Step 352, a cell culture medium exchanging step is performed, wherein the cell culture medium of the cell culture chip 140 is exchanged with the cell culture medium of the first fluid storage unit 111 by the fluid drive unit 160, and the exchanged cell culture medium can be further discharged from the fluid storage device 110 and collected so as to facilitate the following experiments and analysis.

Furthermore, although not shown in the figures, the cell culture method 300 can further include a step which is repeating the cell culture medium replacing step, so that a survival time of the cell in the cell culture chip 140 can be elongated. In detail, the cell culture medium must be exchanged for many times during the period of cell culture so as to make sure that the cell metabolites can be removed effectively and enough nutrients can be supplied to the cell. Therefore, the demands for removing cell metabolites and supplying enough nutrients can be achieved by repeating the cell culture medium replacing step so that the cell can be cultured by the cell culture method 300 of the present disclosure effectively.

Figure 7:
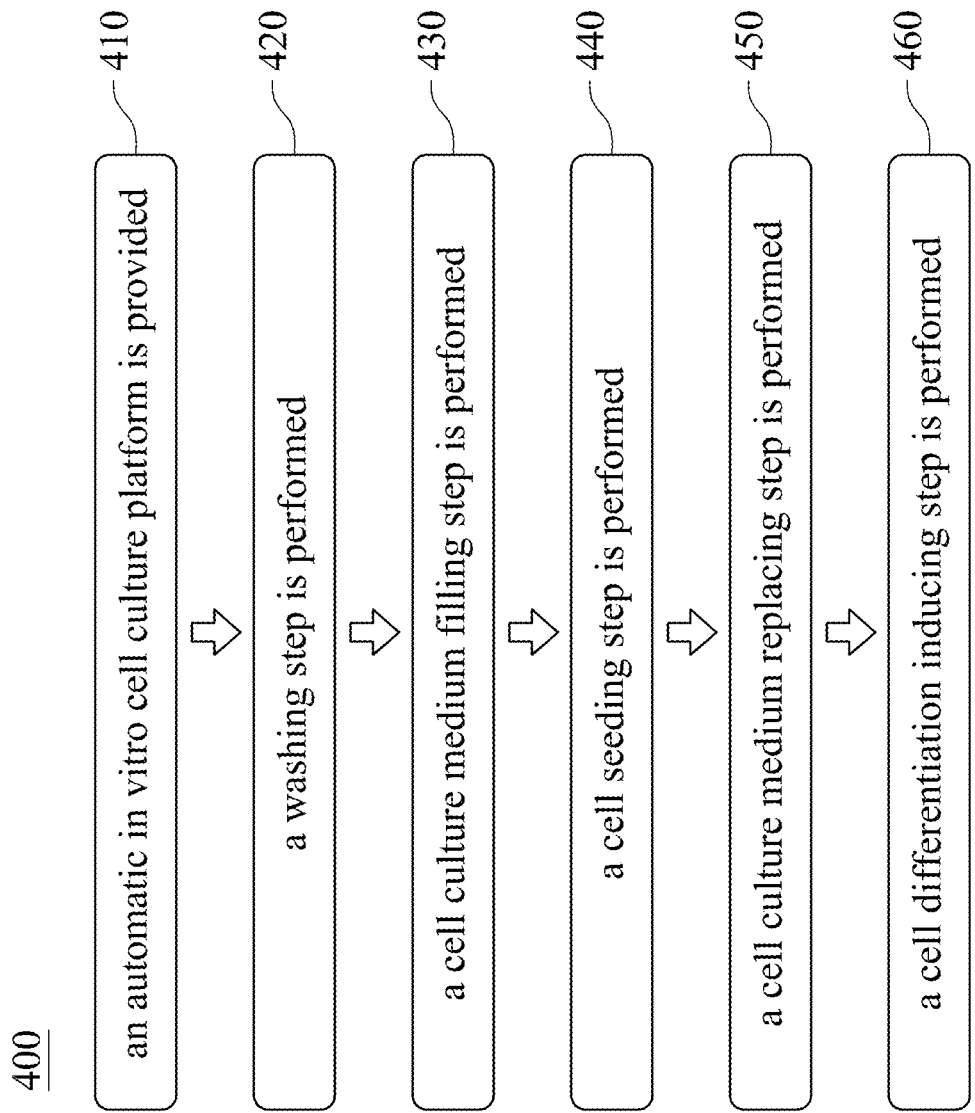
FIG. 7 is a flow chart of a cell culture method according to another embodiment of another aspect of the present disclosure.

Please refer to FIG. 7, which is a flow chart of a cell culture method 400 according to another embodiment of another aspect of the present disclosure. The cell culture method 400 includes Step 410, Step 420, Step 430, Step 440, Step 450 and Step 460. The cell culture method 400 of FIG. 7 and the cell culture method 300 of FIG. 6 are similar in the method and in the process, and the same process and details are not be described again.

In Step 410, the automatic in vitro cell culture platform 100 is provided so as to provide a culture space of the cell in vitro.

In Step 420, a washing step is performed, wherein the cell culture medium is transported from the first fluid storage unit 111 (reference number is shown in FIG. 2) to the cell culture chip 140 by the fluid drive unit 160 so as to wash the upper chamber 141 (reference number is shown in FIG. 5C) and the lower chamber 142 (reference number is shown in FIG. 5C), and then the cell culture medium used to wash the upper chamber 141 and the lower chamber 142 is transported from the cell culture chip 140 to the second fluid storage unit 112 (reference number is shown in FIG. 2) by the fluid drive unit 160.

In Step 430, a cell culture medium filling step is performed, wherein the cell culture medium is transported from the first fluid storage unit 111 to the cell culture chip 140 by the fluid drive unit 160 so as to fill the cell culture medium into the upper chamber 141 and the lower chamber 142, respectively.

In Step 440, a cell seeding step is performed, wherein the cell is seeded in the upper chamber 141 for an incubation time, and the cell is attached and grows on the porous semipermeable membrane 143.

In Step 450, a cell culture medium replacing step is performed, wherein the cell culture medium cultured after the incubation time is removed from the cell culture chip 140 by the fluid drive unit 160, and then the cell culture medium of the first fluid storage unit 111 is transported from the first fluid storage unit 111 to the cell culture chip 140 by the fluid drive unit 160.

In Step 460, a cell differentiation inducing step is performed, wherein a growth factor and a cell differentiation factor are added into the cell culture medium, and the cell culture medium including the growth factor and the cell differentiation factor is transported from the first fluid storage unit 111 to the cell culture chip 140 by the fluid drive unit 160 so as to induce the cell to differentiate into a functional cell. In detail, the cell will proliferate and be confluent in the cell culture chip 140 first when the cell culture medium includes the growth factor and the cell differentiation factor, that is, the cell will proliferate to a sufficient cell number so as to begin the differentiation thereof, and then the cell will differentiate into a functional cell directly in the cell culture chip 140 so as to be applied in the following experiments. Therefore, the automatic in vitro cell culture platform 100 of the present disclosure has the potential to be applied in the fields of drug development, drug testing and so on.

The present disclosure will be further exemplified by the following specific embodiments so as to facilitate utilizing and practicing the present disclosure completely by the people skilled in the art without over-interpreting and over-experimenting. However, the readers should understand that the present disclosure should not be limited to these practical details thereof, that is, in some embodiments, these practical details are used to describe how to implement the materials and methods of the present disclosure and are not necessary.

EXPERIMENTS AND EXAMPLES

Figure 8:
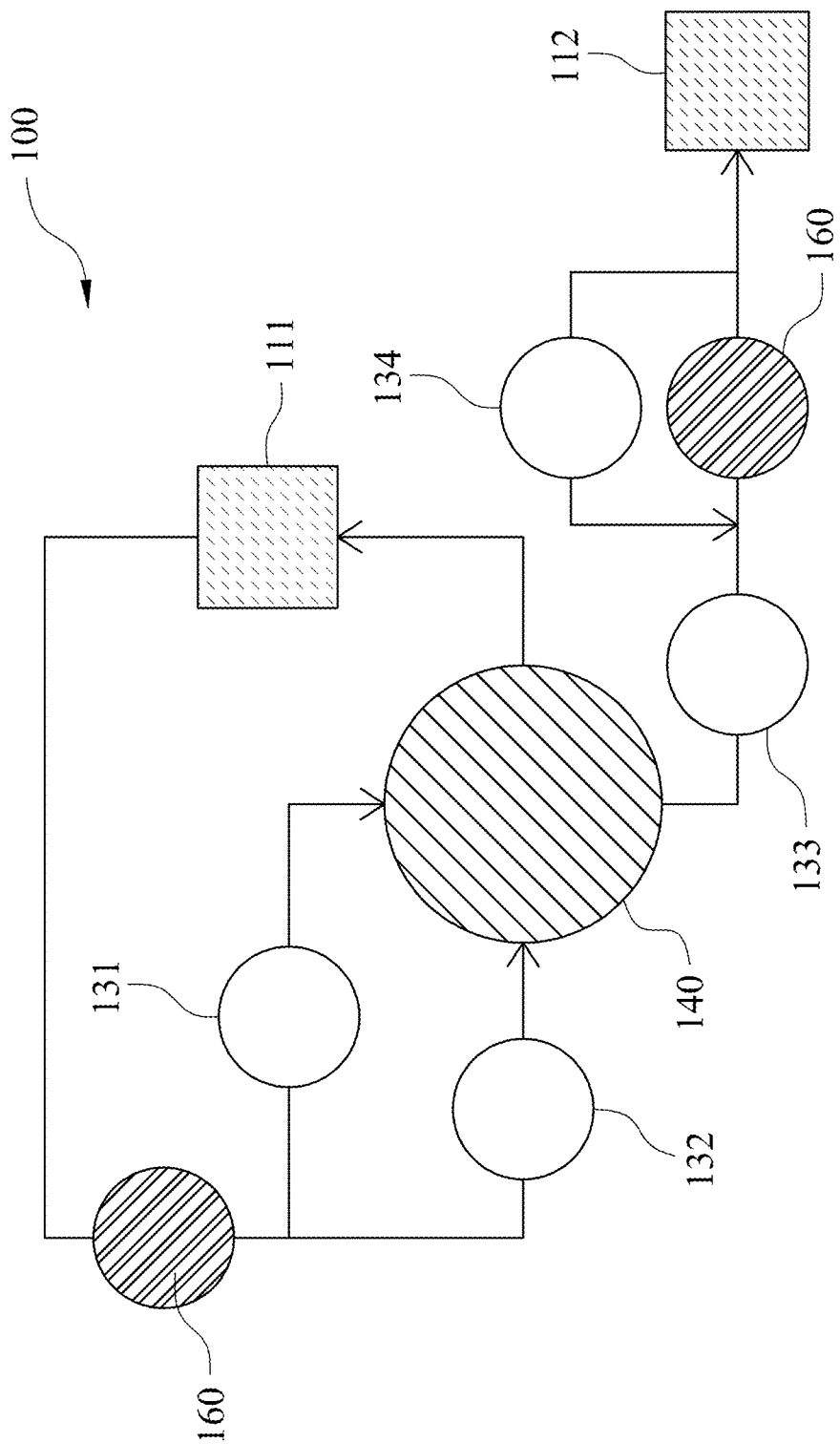
FIG. 8 is a process diagram of the automatic in vitro cell culture platform of FIG. 1.

I. The Automatic In Vitro Cell Culture Platform of the Present Disclosure and the Cell Culture Method Thereof Please refer to FIG. 1, FIG. 6 and FIG. 8, wherein FIG. 8 is a process diagram of the automatic in vitro cell culture platform 100 of FIG. 1. Particularly, FIG. 8 is for illustrating one of the connection arrangements of the fluid drive unit 160, the first valve element 131, the second valve element 132, the third valve element 133, the fourth valve element 134, the cell culture chip 140, the first fluid storage unit 111 and the second fluid storage unit 112 so as to describe the operation method and the workflow of the automatic in vitro cell culture platform 100 in more detail with reference to FIG. 8 and the cell culture method 300 of FIG. 6.

Hereinafter, the operation method and workflow of the automatic in vitro cell culture platform 100 of FIG. 1 and the cell culture method 300 of FIG. 6 will be described in detail with reference to FIG. 8 and Table 1. Table 1 shows the operating conditions of the fluid drive unit 160, the first valve element 131, the second valve element 132, the third valve element 133 and the fourth valve element 134 when Step 310, Step 320, Step 330, Step 340, as well as Step 351 and Step 352 of Step 350 of the cell culture method 300 are performed so as to illustrate the details of the automatic in vitro cell culture platform 100 and the cell culture method 300.

TABLE 1

|  | First valve element | Second valve element | Third valve element | Fourth valve element | Fluid drive unit |
| --- | --- | --- | --- | --- | --- |
| Step 310 | — | — | — | — | — |
| Step 320 | Open | Open | Open | Close | ON |
| Step 330 | Close | Open | Close | Open | ON |
| Step 340 | Close | Open | Close | Open | OFF |
| Step 351 | Close | Open | Open | Close | ON |
| Step 352 | Close | Open | Close | Open | ON |

First, when Step 310 is performed, the automatic in vitro cell culture platform 100 will be provided so as to be applied in the cell culture. At this time, the fluid drive unit 160, the first valve element 131, the second valve element 132, the third valve element 133 and the fourth valve element 134 have not yet started work.

Next, when Step 320 is performed, the cell culture medium will flow through the upper chamber 141 and the lower chamber 142 by the fluid drive unit 160 and wash the upper chamber 141 and the lower chamber 142, and then the aforementioned cell culture medium can be transported from the cell culture chip 140 to the second fluid storage unit 112. At this time, the first valve element 131, the second valve element 132 and the third valve element 133 are open, the fourth valve element 134 is close, and the fluid drive unit 160 is on. In detail, in the embodiment of FIG. 1, the fluid drive unit 160 can be used to control the fluid transportation between the first fluid storage unit 111 and the cell culture chip 140, as well as the fluid transportation between the cell culture chip 140 and the second fluid storage unit 112, so that the cell culture medium can be transported from the first fluid storage unit 111 to the cell culture chip 140. Furthermore, when the fourth valve element 134 is close, the cell culture medium can be directly transported to the cell culture chip 140 through the first valve element 131 and the second valve element 132 and then be transported from the cell culture chip 140 to the second fluid storage unit 112 through the third valve element 133 so as to wash the upper chamber 141 and the lower chamber 142 effectively. Therefore, it is favorable for the subsequent cell culture.

Next, when Step 330 is performed, the cell culture medium will be transported from the first fluid storage unit 111 to the cell culture chip 140 by the fluid drive unit 160. At this time, the first valve element 131 and the third valve element 133 are close, the second valve element 132 and the fourth valve element 134 are open, and the fluid drive unit 160 is on, so that the cell culture medium can be filled to the upper chamber 141 and the lower chamber 142 through the second valve element 132 being open. Furthermore, the third valve element 133 being close can prevent the cell culture medium from being transported to the second fluid storage unit 112 by the fluid drive unit 160. Moreover, because the third valve element 133 is close, the cell culture medium cannot be transported from the cell culture chip 140 to the second fluid storage unit 112 through the third valve element 133. At this time, the fourth valve element 134 being open can restrict the fluid to flow within the tube disposed among the fourth valve element 134, the cell culture chip 140 and the second fluid storage unit 112 corresponding to the working of the fluid drive unit 160, so that the damage of the tubes due to the idling of fluid drive unit 160 can be avoided. Therefore, the fluid transportation between the first fluid storage unit 111 and the cell culture chip 140, as well as the fluid transportation between the cell culture chip 140 and the second fluid storage unit 112 can be controlled by the fluid drive unit 160 simultaneously, so that the use efficiency of the fluid drive unit 160 can be maximized.

Next, when Step 340 is performed, the cell will be seeded in the upper chamber 141 and then attach and grow on the porous semipermeable membrane 143. At this time, the first valve element 131 and the third valve element 133 are close, the second valve element 132 and the fourth valve element 134 are open, and the fluid drive unit 160 is off so as to facilitate the user to seed the cell in the upper chamber 141. Furthermore, when the third valve element 133 is close, it is favorable for preventing the cell culture medium including the cell which has not attached to the porous semipermeable membrane 143 from leaking from the second fluid storage unit 112 so as to enhance the efficiency of cell seeding and controlling the seeding number of the cell.

Next, when Step 351 is performed, the first valve element 131 and the fourth valve element 134 are close, the second valve element 132 and the third valve element 133 are open, and the fluid drive unit 160 is on, so that the cell culture medium cultured after the incubation time can be transported from the upper chamber 141 to the second fluid storage unit 112 by the fluid drive unit 160 through the third valve element 133 being open, and then the cell culture medium of the first fluid storage unit 111 can be transported to and fill the cell culture chip 140 by the fluid drive unit 160 through the second valve element 132 being open. Therefore, the cell culture medium including cell metabolites, aging cells and other wastes can be removed so that a new cell culture medium can be further added so as to provide enough nutrients needed for cell growth.

Furthermore, when Step 352 is performed, the cell culture medium of the cell culture chip 140 can be exchanged with the cell culture medium of the first fluid storage unit 111 by the fluid drive unit 160. At this time, the first valve element 131 and the third valve element 133 are close, and the second valve element 132 and the fourth valve element 134 are open. Therefore, it is favorable for preventing the cell culture medium from being transported to the second fluid storage unit 112 through the third valve element 133 so as to exchange and collect the cell culture medium.

According to the aforementioned description, in the automatic in vitro cell culture platform 100 of the present disclosure, the cell culture medium can be transported automatically among the fluid storage device 110, the channel control panel 120 and the cell culture chip 140 by the controlling of the first valve element 131, the second valve element 132, the third valve element 133, the fourth valve element 134 and the fluid drive unit 160. Therefore, it is favorable for not only avoiding the difference of cell culture state or contamination caused by human manipulation but also enhancing the cell culture efficiency, the stability and the potentials for applying to the fields of drug development or other experiments.

II. Efficiency Test of the Automated Cell Culture of the Automatic In Vitro Cell Culture Platform of the Present Disclosure The automatic in vitro cell culture platform 100 of FIG. 1 and the cell culture method 300 of FIG. 6 are used to culture the human bronchial epithelial cells (HBEC3 KT) so as to test the efficiency of the automatic in vitro cell culture platform of the present disclosure for culturing the cell automatically. In detail, the growth status of the human bronchial epithelial cells in the automatic in vitro cell culture platform 100 will be observed so as to estimate the cell culture ability and the efficiency thereof of the automatic in vitro cell culture platform 100 of the present disclosure.

1. The Cell Culture and Growth Test of the Human Bronchial Epithelial Cells Cultured in the Automatic In Vitro Cell Culture Platform of the Present Disclosure The present experiment includes Example 1 and a positive control group, wherein the human bronchial epithelial cells of Example 1 are cultured in the automatic in vitro cell culture platform 100. In this experiment, the human bronchial epithelial cells of Example 1 are seeded in the cell culture chip 140 of the automatic in vitro cell culture platform 100 in a number of $2 \times 10^5$ cells and incubated in the incubator at 37° C. with 5% $CO_2$, and the human bronchial epithelial cells of the positive control group are seeded in the 6-well Transwell® plate (Corning, Specification 3450) in a density of $2 \times 10^5$ cells per well and also incubated in the incubator at 37° C. with 5% $CO_2$. The growth status of the human bronchial epithelial cells of Example 1 and the positive control group will be observed by the microscope after incubating for 1 day and 3 days.

Figure 9:
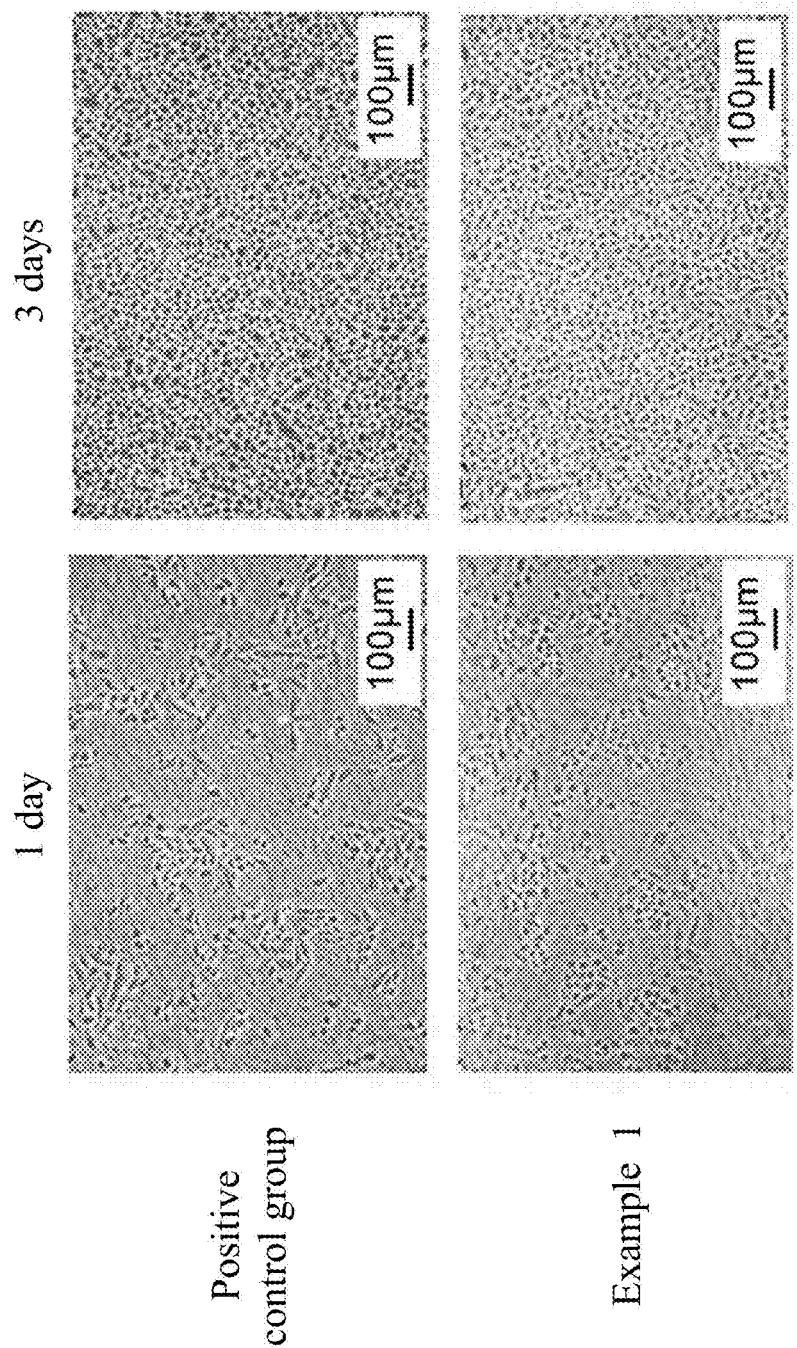
FIG. 9 is a microscope image diagram of the human bronchial epithelial cells of Example 1 and a positive control group after incubating for 1 day and 3 days.

Please refer to FIG. 9, which is a microscope image diagram of the human bronchial epithelial cells of Example 1 and the positive control group after incubating for 1 day and 3 days. As shown in FIG. 9, the human bronchial epithelial cells of Example 1 have attached and grown on the porous semipermeable membrane 143 after incubating for 1 day and has been confluent in the growing space of the automatic in vitro cell culture platform 100 after incubating for 3 days, and the human bronchial epithelial cells of the positive control group also have been confluent in the growing space of the Transwell® plate after incubating for 3 days. As shown in the aforementioned results, the human bronchial epithelial cells can proliferate and grow in the automatic in vitro cell culture platform 100 of the present disclosure, and the growth status and proliferating time thereof are similar with the human bronchial epithelial cells cultured in the marketed cell culture device which should be operated manually. Accordingly, the automatic in vitro cell culture platform 100 of the present disclosure can effectively automatically culture cells, and both of the growth state and proliferation ability of the cells cultured therein are excellent.

2. The Cell Differentiation Test of the Human Bronchial Epithelial Cells Cultured in the Automatic In Vitro Cell Culture Platform of the Present Disclosure The present experiment includes Example 2 and a positive control group, wherein the human bronchial epithelial cells of Example 2 are cultured in the automatic in vitro cell culture platform 100. Both of the cell culture medium of Example 2 and the positive control group include the growth factor and the cell differentiation factor, wherein the aforementioned cell differentiation factor includes transferrin, triiodothyronine and hydrocortisone.

In this experiment, the human bronchial epithelial cells of Example 2 are seeded in the cell culture chip 140 of the automatic in vitro cell culture platform 100 in a number of $2 \times 10^5$ cells and incubated in the incubator at 37° C. with 5% $CO_2$, and the human bronchial epithelial cells of the positive control group are seeded in the 6-well Transwell® plate in a density of $2 \times 10^5$ cells per well and also incubated in the incubator at 37° C. with 5% $CO_2$. The growth status and the cell differentiation status of the human bronchial epithelial cells of Example 2 and the positive control group will be observed by the microscope after incubating for 4 days, 7 days and 13 days.

Figure 10A:
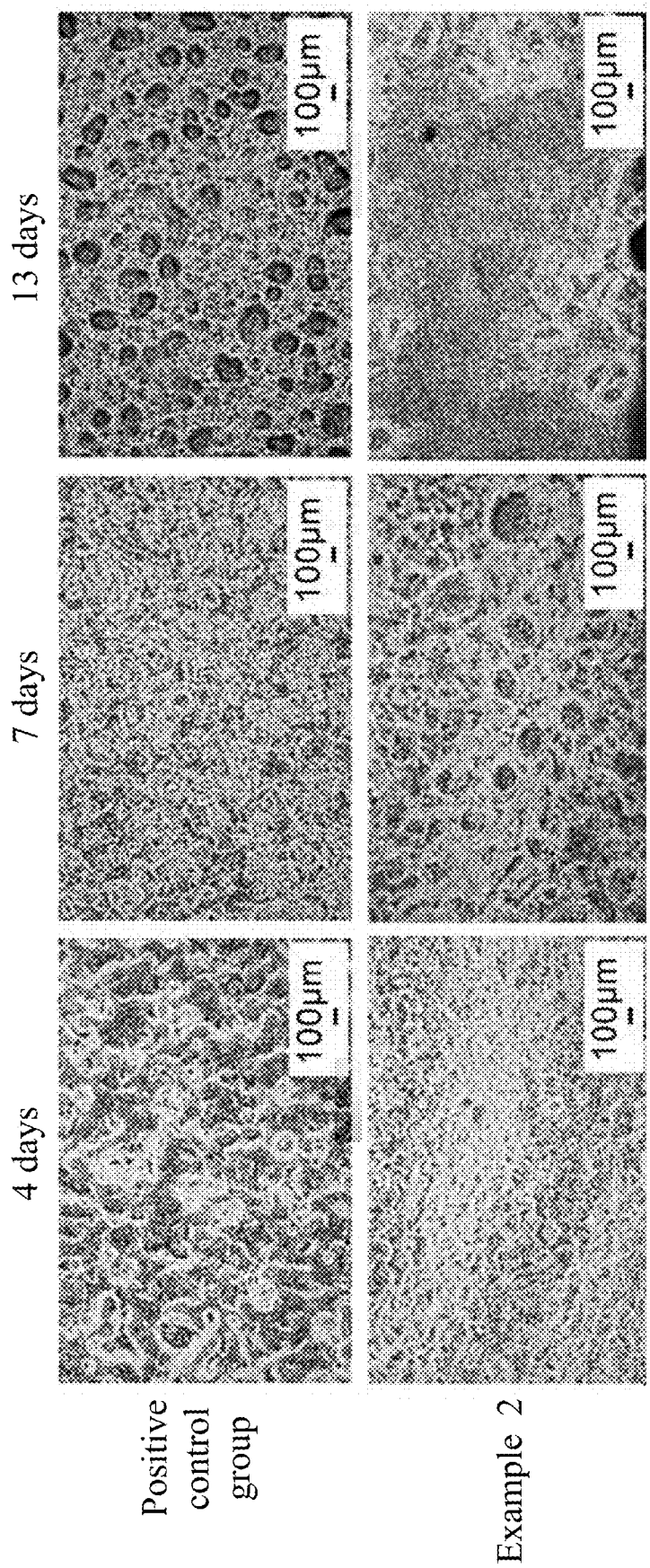
FIG. 10A is a microscope image diagram in four times magnification of the human bronchial epithelial cells of Example 2 and a positive control group after incubating for 4 days, 7 days and 13 days.
Figure 10B:
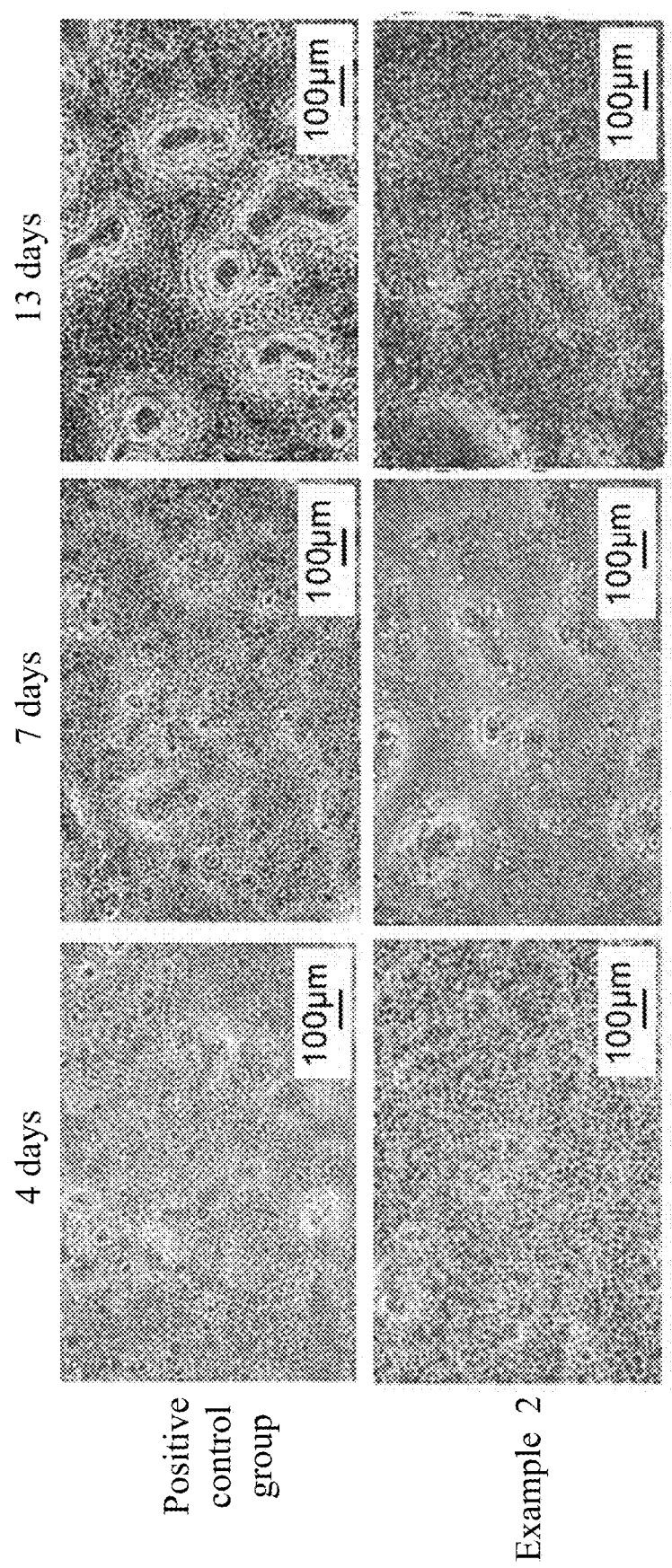
FIG. 10B is a microscope image diagram in ten times magnification of the human bronchial epithelial cells of Example 2 and the positive control group after incubating for 4 days, 7 days and 13 days.

Please refer to FIG. 10A and FIG. 10B, wherein FIG. 10A is a microscope image diagram in four times magnification of the human bronchial epithelial cells of Example 2 and the positive control group after incubating for 4 days, 7 days and 13 days, and FIG. 10B is a microscope image diagram in ten times magnification of the human bronchial epithelial cells of Example 2 and a positive control group after incubating for 4 days, 7 days and 13 days. As shown in FIG. 10A and FIG. 10B, the human bronchial epithelial cells of Example 2 have started to differentiate after incubating for 4 days and then differentiated to different types of functional cells as the increase of the incubation time. Furthermore, an outer contour of the goblet cells which can secrete mucus can be found in the human bronchial epithelial cells of Example 2 after incubating for 7 days, and after incubating for 13 days, the differentiated human bronchial epithelial cells have already grown and reached about 80% confluence in the automatic in vitro cell culture platform 100, and clumps of stacked cells have also appeared (that is, the area defined by the red dotted line in FIG. 10B). As for the positive control group, the human bronchial epithelial cells of the positive control group have started to differentiate after incubating for 4 days, wherein an outer contour of the goblet cells which can secrete mucus can be found after incubating for 7 days, and the differentiated human bronchial epithelial cells also can be found clearly in the microscope image after incubating for 13 days.

As shown in the aforementioned results, the human bronchial epithelial cells can grow and differentiate in the automatic in vitro cell culture platform 100 of the present disclosure, and the differentiation status and differentiating time thereof are similar with the human bronchial epithelial cells cultured in the marketed cell culture device which should be operated manually. Accordingly, the automatic in vitro cell culture platform 100 of the present disclosure can effectively automatically culture cells, and the cells cultured therein not only have excellent growth and proliferation abilities, but also can differentiate into functional cells effectively in the presence of the growth factor and the cell differentiation factor. Therefore, the automatic in vitro cell culture platform 100 of the present disclosure has the potential to be applied in the related experiments.

3. The Cell Differentiation Ability Test of the Human Bronchial Epithelial Cells In Vivo in the Automated In Vitro Cell Culture Platform of the Present Disclosure Which is Used to Simulate the Growth Conditions The present experiment includes Example 3, wherein the human bronchial epithelial cells of Example 3 are cultured in the automatic in vitro cell culture platform 100. The cell culture medium of Example 3 includes the growth factor and the cell differentiation factor, wherein the aforementioned cell differentiation factor includes transferrin, triiodothyronine and hydrocortisone.

In this experiment, the human bronchial epithelial cells of Example 3 are seeded in the cell culture chip 140 of the automatic in vitro cell culture platform 100 in a number of $2 \times 10^5$ cells and incubated in the incubator at 37° C. with 5% $CO_2$ for three days. Next, the cell culture medium of the upper chamber 141 is removed so that the surface of the human bronchial epithelial cells can be exposed to the air directly so as to simulate the growth conditions thereof in vivo. And then, the human bronchial epithelial cells are cultured continuously for 5 days, 7 days and 10 days so as to observe the differentiation condition of the human bronchial epithelial cells in the automatic in vitro cell culture platform 100.

Figure 11A:
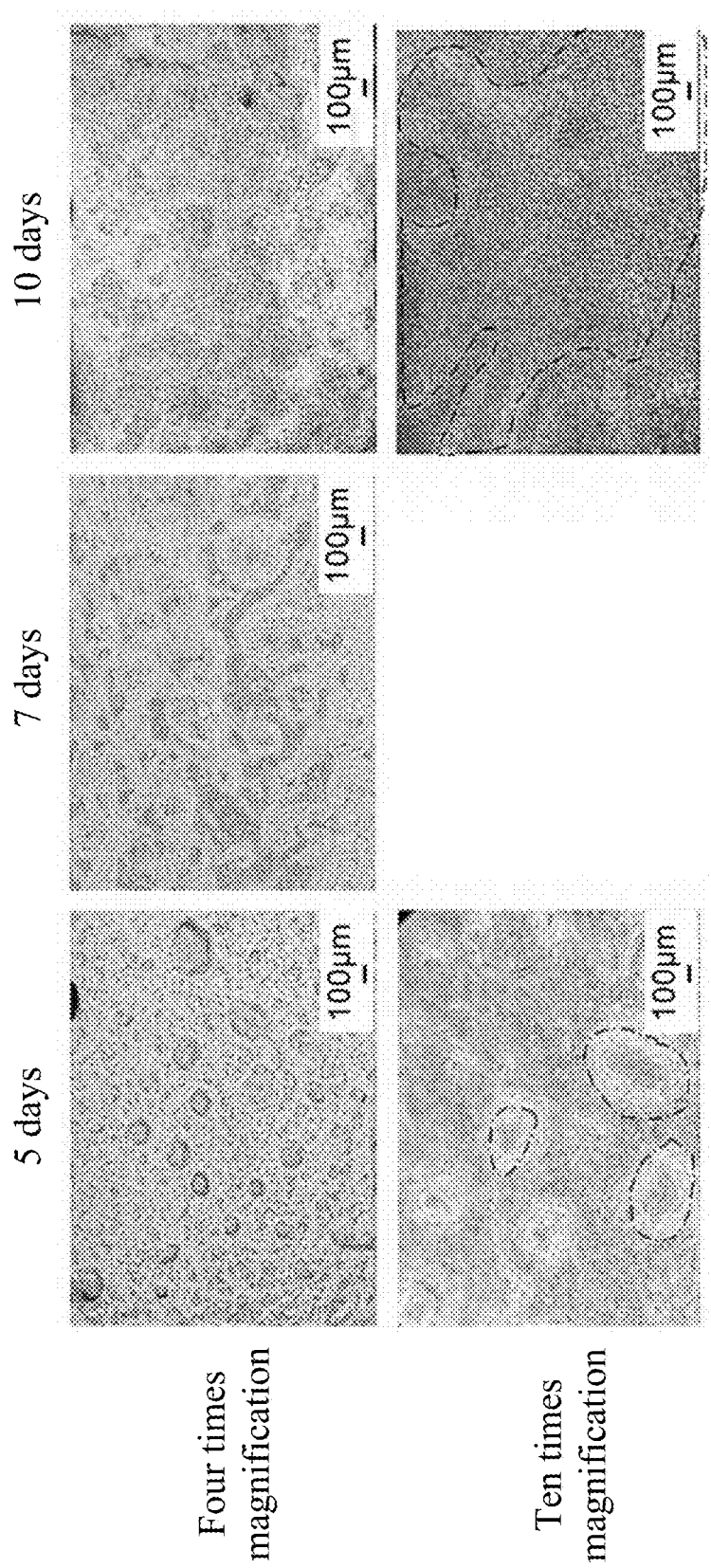
FIG. 11A is a tissue staining image diagram of the human bronchial epithelial cells of Example 3 exposed to the air for 5 days, 7 days and 10 days.

Please refer to FIG. 11A, which is a tissue staining image diagram of the human bronchial epithelial cells of Example 3 exposed to the air for 5 days, 7 days and 10 days. As shown in FIG. 11A, an outer contour of the goblet cells which can secrete mucus can be found in the human bronchial epithelial cells of Example 3 (that is, the area defined by the dotted line in the ten times magnification image of FIG. 11A) after being exposed to the air and incubating for 5 days, and the human bronchial epithelial cells will gradually differentiate into functional cells with different functions along the increase of the culture time exposed to the air. Furthermore, the differentiated human bronchial epithelial cells can be found clearly after being exposed to the air and incubating for 10 days, and clumps of stacked cells have also appeared thereon (that is, the area defined by the dotted line in the ten times magnification image of FIG. 11A).

Figure 11B:
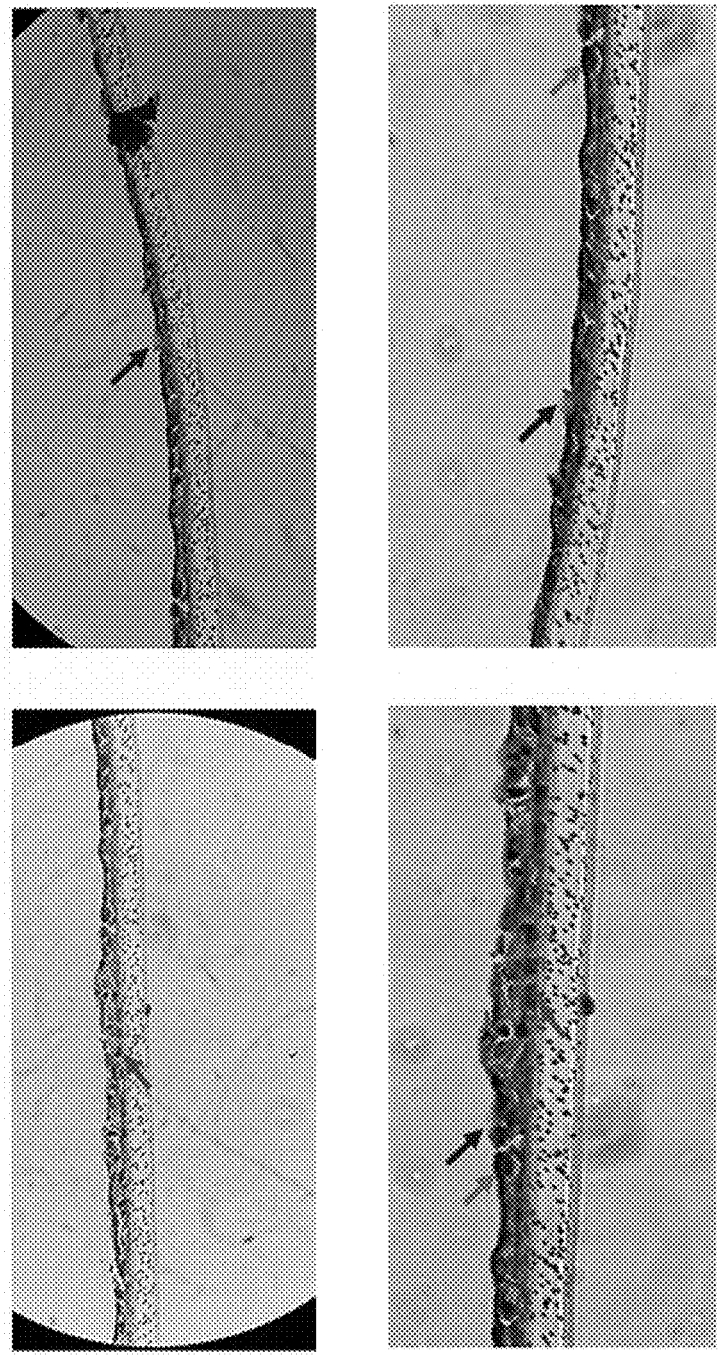
FIG. 11B is a histologic section image diagram of the human bronchial epithelial cells of Example 3 exposed to the air for 28 days.

Please refer to FIG. 11B, which is a histologic section image diagram of the human bronchial epithelial cells of Example 3 exposed to the air for 28 days. In FIG. 11B, the cells pointed by the red arrow are basal cells differentiated from the human bronchial epithelial cells, the cells pointed by the green arrow are goblet cells differentiated from the human bronchial epithelial cells, and the cells pointed by the blue arrow are cilia cells differentiated from the human bronchial epithelial cells. As shown in FIG. 11B, after being exposed to the air and incubating for 28 days, the basal cells can be found in the lower layer of the bronchial tissue differentiated from the human bronchial epithelial cells of Example 3 (as shown in the top left image of FIG. 11B), the cilia cells can be found on the surface of the bronchial tissue (that is, the cell surface directly exposed to the air) differentiated from the human bronchial epithelial cells (as shown in the top right image of FIG. 11B). Furthermore, as shown in the bottom left image and the bottom right image of FIG. 11B, the basal cell can be found in the lowest layer of the bronchial tissue differentiated from the human bronchial epithelial cells, the goblet cells can be found in a layer upon the aforementioned lowest layer, and the cilia cells can be found on the surface of the bronchial tissue with the cilia thereof being outward.

As shown in the aforementioned results, the automatic in vitro cell culture platform 100 of the present disclosure can simulate the growth conditions of the human bronchial epithelial cells in vivo and can effectively promote the human bronchial epithelial cells to differentiate continuously, so that the human bronchial epithelial cells can differentiate continuously so as to form the bronchial tissue outside the human body. Therefore, the automatic in vitro cell culture platform 100 of the present disclosure has the potential to apply to related experiments.

According to the aforementioned examples, the automatic in vitro cell culture platform and the cell culture method of the present disclosure can automatically transport the cell culture medium among the fluid storage device, the channel control panel and the cell culture chip by the fluid drive unit. It is favorable for eliminate the steps for changing the cell culture medium manually during cell culture or the experiment so as to prevent the difference of cell culture state or contamination caused by human manipulation but also enhance safety, efficiency and stability of cell culture. Furthermore, the growth factor and the cell differentiation factor can be added into the cell medium during the cell culture, so that the cells can differentiate into the functional cells and then form a primary tissue thereof in the automatic in vitro cell culture platform of the present disclosure. Therefore, the automatic in vitro cell culture platform of the present disclosure can be further applied in the fields, such as cell culture, drug development and drug safety testing, and the market value thereof is also excellent.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An in vitro cell culture platform, comprising:
    a fluid storage device, comprising:
        a first fluid storage unit for storing a cell culture medium; and
        a second fluid storage unit disposed adjacent to the first fluid storage unit and for storing a waste liquid;
    a channel control panel comprising a plurality of channel ports, a plurality of connecting tubes and a valve group, wherein the channel control panel is pipe-connected to the fluid storage device by the connecting tubes, and the valve group is for controlling a transport of the cell culture medium and the waste liquid;
    a cell culture chip having a pipe connection surface and disposed on the channel control panel, and the cell culture chip comprising:
        an upper chamber for culturing a cell;
        a lower chamber disposed under the upper chamber and for accommodating the cell culture medium;
        a porous semipermeable membrane disposed between the upper chamber and the lower chamber, wherein the cell culture medium can flow between the upper chamber and the lower chamber through the porous semipermeable membrane, a liquid level of the cell culture medium in the cell culture chip is higher than a level of the porous semipermeable membrane in the cell culture chip, and an average pore size of the porous semipermeable membrane ranges from 0.2 µm to 8 µm;
        at least four pipe ports separately disposed on the pipe connection surface; and
        at least four infusion tubes, wherein the cell culture chip is pipe-connected to the channel control panel by the infusion tubes, one end of each of the infusion tubes is connected correspondingly to one of the pipe ports, and the other end of each of the infusion tubes is connected to the channel control panel; and
    a fluid drive unit pipe-connected to the channel control panel and for driving the cell culture medium and the waste liquid to flow between the fluid storage device and the cell culture chip through the channel control panel;
    wherein the channel control panel has a tube connection surface, the channel ports are separately disposed on the tube connection surface, one end of each of the connecting tubes is connected correspondingly to one of the channel ports, and the other end of each of the connecting tubes is connected to the fluid drive unit or the fluid storage device.

2. The in vitro cell culture platform of claim 1, wherein the cell culture chip comprises, in order from the pipe connection surface to a bottom of the cell culture chip:
    a first base plate comprising an opening, wherein the pipe connection surface is disposed on the first base plate;
    a second base plate comprising an opening;
    a third base plate comprising an opening, wherein the porous semipermeable membrane is disposed and covered on the opening;
    a fourth base plate comprising an opening; and
    a resin sheet;
    wherein the first base plate, the second base plate and the third base plate are sequentially stacked and the opening of the first base plate corresponds to the opening of the second base plate and the porous semipermeable membrane so as to form the upper chamber, the upper chamber is opened on the pipe connection surface, the third base plate, the fourth base plate and the resin sheet are sequentially stacked and the opening of the third base plate corresponds to the opening of the fourth base plate and the resin sheet so as to form the lower chamber, and the lower chamber is connected to the first base plate though holes of the second base plate and the third base plate and is opened on the pipe connection surface.

3. The in vitro cell culture platform of claim 2, wherein two of the pipe ports are opened holes of the upper chamber, and the other two of the pipe ports are opened holes of the lower chamber.

4. The in vitro cell culture platform of claim 2, wherein the first base plate, the second base plate, the third base plate, the fourth base plate and the resin sheet are made by a laser cutting method.

5. The in vitro cell culture platform of claim 1, wherein the valve group comprises a plurality of valve elements for controlling the transport of the cell culture medium and the waste liquid, respectively.

6. The in vitro cell culture platform of claim 1, wherein the channel control panel comprises, in order from the tube connection surface to a bottom of the channel control panel:
    a tube connection plate, wherein the tube connection surface is disposed on the tube connection plate;
    a first channel base plate;
    a second channel base plate;
    a third channel base plate; and
    a bottom plate;
    wherein the tube connection plate, the first channel base plate, the second channel base plate, the third channel base plate and the bottom plate are sequentially stacked so as to form a plurality of microchannels for transporting the cell culture medium and the waste liquid, and the microchannels are opened on the tube connection surface.

7. The in vitro cell culture platform of claim 6, wherein the tube connection plate, the first channel base plate, the second channel base plate, the third channel base plate and the bottom plate are made by a laser cutting method.

8. The in vitro cell culture platform of claim 1, wherein the fluid storage device further comprises a medium exchange port and a waste liquid exchange port, the medium exchange port is connected to the first fluid storage unit, and the waste liquid exchange port is connected to the second fluid storage unit.

9. The in vitro cell culture platform of claim 1, wherein the fluid drive unit is a peristaltic pump.

10. The in vitro cell culture platform of claim 1, wherein the cell culture medium comprises a growth factor and a cell differentiation factor.

11. The in vitro cell culture platform of claim 1, wherein the first fluid storage unit comprises:
 a plurality of fluid storage subunits separately disposed in the first fluid storage unit.

12. The in vitro cell culture platform of claim 1, further comprising:
 a basal board, which is substantially a rectangle, wherein the fluid storage device, the channel control panel, the channel control panel, the cell culture chip and the fluid drive unit are disposed on the basal board.

13. A cell culture method, comprising:
 providing the in vitro cell culture platform of claim 1;
 performing a washing step, wherein the cell culture medium is transported from the first fluid storage unit to the cell culture chip by the fluid drive unit so as to wash the upper chamber and the lower chamber, and then the cell culture medium used to wash the upper chamber and the lower chamber is transported from the cell culture chip to the second fluid storage unit by the fluid drive unit;
 performing a cell culture medium filling step, wherein the cell culture medium is transported from the first fluid storage unit to the cell culture chip by the fluid drive unit so as to fill the cell culture medium into the upper chamber and the lower chamber, respectively;
 performing a cell seeding step, wherein the cell is seeded in the upper chamber for an incubation time, and the cell is attached and grows on the porous semipermeable membrane; and
 performing a cell culture medium replacing step, wherein the cell culture medium cultured after the incubation time is removed from the cell culture chip by the fluid drive unit, and then the cell culture medium of the first fluid storage unit is transported from the first fluid storage unit to the cell culture chip by the fluid drive unit.

14. The cell culture method of claim 13, wherein the cell culture medium replacing step comprises:
 performing an upper-chambered cell culture medium removing step, wherein the cell culture medium cultured after the incubation time is transported from the upper chamber to the second fluid storage unit by the fluid drive unit, and then the cell culture medium of the first fluid storage unit is transported to the cell culture chip by the fluid drive unit; and
 performing a cell culture medium exchanging step, wherein the cell culture medium of the cell culture chip is exchanged with the cell culture medium of the first fluid storage unit by the fluid drive unit.

15. The cell culture method of claim 13, further comprising:
 repeating the cell culture medium replacing step for elongating a survival time of the cell in the cell culture chip.

16. The cell culture method of claim 13, further comprising:
 performing a cell differentiation inducing step, wherein a growth factor and a cell differentiation factor are added into the cell culture medium, and the cell culture medium comprising the growth factor and the cell differentiation factor is transported from the first fluid storage unit to the cell culture chip by the fluid drive unit so as to induce the cell to differentiate into a functional cell.

* * * * *